(12) United States Patent
Tenney et al.

(10) Patent No.: US 8,709,396 B2
(45) Date of Patent: *Apr. 29, 2014

(54) METHOD AND COMPOSITION FOR ATTRACTING ARTHROPODS BY VOLATIZING AN ACID

(75) Inventors: Joel Tenney, Marietta, GA (US); Tom Isaac, Newnan, GA (US); William Ernst, Roswell, GA (US)

(73) Assignee: Premark FEG L.L.C., Wilmington, DE (US)

(*) Notice: Subject to any disclaimer, the term of this patent is extended or adjusted under 35 U.S.C. 154(b) by 1548 days.

This patent is subject to a terminal disclaimer.

(21) Appl. No.: 12/032,885

(22) Filed: Feb. 18, 2008

(65) Prior Publication Data

US 2008/0138372 A1 Jun. 12, 2008

Related U.S. Application Data

(60) Division of application No. 10/661,724, filed on Sep. 12, 2003, now Pat. No. 7,347,994, which is a continuation-in-part of application No. 10/243,590, filed on Sep. 13, 2002, now Pat. No. 7,922,992.

(51) Int. Cl.
| | |
|---|---|
| A01N 25/08 | (2006.01) |
| A01N 25/12 | (2006.01) |
| A01N 59/04 | (2006.01) |
| A01N 59/16 | (2006.01) |
| A01N 37/02 | (2006.01) |
| A01P 19/00 | (2006.01) |

(52) U.S. Cl.
USPC ............ 424/84; 424/409; 424/647; 424/666; 424/700; 424/715; 424/716; 424/717; 514/557; 43/132.1

(58) Field of Classification Search
USPC .......... 424/84, 409, 647, 666, 700, 715, 716, 424/717; 514/557
See application file for complete search history.

(56) References Cited

U.S. PATENT DOCUMENTS

| | | | |
|---|---|---|---|
| 2,163,793 A | 6/1939 | Logan | |
| 2,482,891 A | 9/1949 | Aston | |
| 2,885,368 A | 5/1959 | Hess et al. | |
| 3,049,399 A | 8/1962 | Gamson et al. | |
| 3,271,242 A | 9/1966 | McNicholas | |
| 3,298,780 A | 1/1967 | Fleck | |
| 3,382,033 A | 5/1968 | Kitagawa | |
| 3,997,462 A | 12/1976 | Denaeyer et al. | |
| 4,247,531 A | 1/1981 | Hicks | |
| 4,528,171 A | 7/1985 | Casci et al. | |
| 4,547,381 A | 10/1985 | Mason et al. | |
| 4,554,261 A | 11/1985 | Gergely et al. | |
| 4,581,219 A | 4/1986 | Imada et al. | |
| 4,585,482 A | 4/1986 | Tice et al. | |
| 4,590,057 A | 5/1986 | Hicks | |
| 4,610,882 A | 9/1986 | Laurent et al. | |
| 4,689,169 A | 8/1987 | Mason et al. | |
| 4,695,296 A | 9/1987 | Christe | |
| 4,731,193 A | 3/1988 | Mason et al. | |
| 4,815,092 A | 3/1989 | Chartier | |
| 4,844,981 A | 7/1989 | Landau | |
| 4,871,701 A | 10/1989 | Danner et al. | |
| 4,889,654 A | 12/1989 | Mason et al. | |
| 5,264,227 A | 11/1993 | Laroche et al. | |
| 5,278,112 A | 1/1994 | Klatte | |
| 5,302,354 A | 4/1994 | Watvedt et al. | |
| 5,346,876 A | 9/1994 | Ichimura et al. | |
| 5,360,609 A | 11/1994 | Wellinghoff | |
| 5,376,164 A | 12/1994 | Zarchy et al. | |
| 5,407,656 A | 4/1995 | Roozdar | |
| 5,458,743 A | 10/1995 | Allen | |
| 5,567,405 A | 10/1996 | Klatte et al. | |
| 5,573,743 A | 11/1996 | Klatte et al. | |
| 5,631,300 A | 5/1997 | Wellinghoff | |
| 5,639,295 A | 6/1997 | Wellinghoff et al. | |
| 5,668,185 A | 9/1997 | Wellinghoff | |
| 5,669,176 A | 9/1997 | Miller | |
| 5,705,092 A | 1/1998 | Wellinghoff et al. | |
| 5,730,948 A | 3/1998 | Klatte et al. | |
| 5,776,850 A | 7/1998 | Klatte et al. | |
| 5,853,689 A | 12/1998 | Klatte | |

(Continued)

FOREIGN PATENT DOCUMENTS

| | | |
|---|---|---|
| EP | 0132049 A1 | 1/1985 |
| EP | 0 423 817 A2 | 4/1991 |

(Continued)

OTHER PUBLICATIONS

Webster's New World Dictionary, $2^{nd}$ college edition, The World Publishing Co., New York, 1972, p. 706.*
Greenwood, N.N. et al. Chemistry of the Elements. Butterworth Henemann, Oxford, 1997, pp. 48-51.*
Masschelein, *Chlorine Dioxide—Chemistry and Environmental Impact of Oxychlorine Compounds* (1979) (Ann Arbor Science Publishers Inc., Ann Arbor, Michigan), pp. 138-141.
Morita, Yasuo et al., "Manufacture of a Solid Chlorine Dioxide Generating Agent," *Chemical Abstracts*, vol. 100, No. 2, Abstract No. 9463, Jan. 9, 1984.
Gao, et al., "Use of Tailored Zeolites for Removal of Benzene and Toluene From Water," 45th Purdue Industrial Waste Conference Proceedings, 1992, pp. 509-515, Lewis Publishers, Inc., Chelsea, Michigan.

(Continued)

*Primary Examiner* — John Pak
(74) *Attorney, Agent, or Firm* — Alston & Bird LLP

(57) ABSTRACT

The invention is a method for attracting mosquitoes by producing a volatilized acid by combining an acid precursor with water to produce the humidified vapor acid attractant, preferably hydrogen chloride. The humidified volatilized acid can be further combined with carbon dioxide, or carbon dioxide can be simultaneously produced to attract mosquitoes. The acid precursor can be a hydrate of ferric chloride, such as ferric chloride hexahydrate. The acid precursor can be impregnated in a carrier, and can be combined with water through exposure to water vapor in the atmosphere, the intentional addition of water, or water produced by a chemical reaction.

8 Claims, No Drawings

(56) References Cited

U.S. PATENT DOCUMENTS

| | | | |
|---|---|---|---|
| 5,885,543 A | 3/1999 | Klatte | |
| 5,965,264 A * | 10/1999 | Barenberg et al. | 428/402 |
| 5,974,810 A | 11/1999 | Speronello | |
| 5,989,497 A | 11/1999 | Labonte, Jr. | |
| 6,055,766 A | 5/2000 | Nolen et al. | |
| 6,077,495 A | 6/2000 | Speronello et al. | |
| 6,106,775 A | 8/2000 | Fuller | |
| 6,174,508 B1 | 1/2001 | Klatte | |
| 6,267,953 B1 | 7/2001 | Bernier et al. | |
| 6,294,108 B1 | 9/2001 | Speronello et al. | |
| 6,379,643 B1 | 4/2002 | Klatte | |
| 6,423,289 B1 | 7/2002 | Klatte | |
| 6,458,735 B1 | 10/2002 | Klatte | |
| 6,503,419 B2 | 1/2003 | Klatte | |
| 6,516,559 B1 | 2/2003 | Simchoni et al. | |
| 6,566,392 B1 | 5/2003 | Okada et al. | |
| 6,592,919 B1 | 7/2003 | Matthews et al. | |
| 6,602,466 B2 | 8/2003 | Hamilton et al. | |
| 6,607,696 B1 | 8/2003 | Hamilton et al. | |
| 2001/0031298 A1 | 10/2001 | Fuller | |
| 2001/0038805 A1 | 11/2001 | Hamilton et al. | |
| 2002/0028191 A1 | 3/2002 | Bernier et al. | |
| 2002/0036284 A1 | 3/2002 | Speronello et al. | |
| 2002/0122813 A1 | 9/2002 | Healy | |
| 2003/0053931 A1 | 3/2003 | Hamilton et al. | |
| 2003/0217503 A1 | 11/2003 | Robison | |
| 2004/0131736 A1 | 7/2004 | Pan et al. | |

FOREIGN PATENT DOCUMENTS

| | | |
|---|---|---|
| EP | 0 527 228 A1 | 2/1993 |
| EP | 0 710 621 A1 | 5/1996 |
| JP | 52038028 | 3/1977 |
| JP | 56067521 | 6/1981 |
| JP | 57125683 A3 | 8/1982 |
| JP | 58 140312 A | 8/1983 |
| JP | 58161904 | 9/1983 |
| JP | 59-98008 A | 6/1984 |
| JP | 60000827 | 1/1985 |
| JP | 61256915 | 11/1986 |
| JP | 01071804 | 3/1989 |
| JP | 02 020270 A | 1/1990 |
| JP | 2198629 | 8/1990 |
| JP | 03000979 A | 1/1991 |
| JP | 3023863 | 1/1991 |
| JP | 6285368 | 10/1994 |
| WO | WO-85/05008 | 11/1985 |
| WO | WO-85/05038 | 11/1985 |
| WO | WO 98/11776 | 3/1998 |
| WO | WO 98/38865 | 9/1998 |
| WO | WO 99/26471 | 6/1999 |
| WO | WO 00/11944 | 3/2000 |
| WO | WO 00/21580 | 4/2000 |
| WO | WO 00/27187 | 5/2000 |
| WO | WO 00/65910 | 11/2000 |
| WO | WO 00/69775 | 11/2000 |
| WO | WO 01/30150 A1 | 5/2001 |
| WO | WO 01/32013 | 5/2001 |
| WO | WO 02/15683 A1 | 2/2002 |
| WO | WO 02/069723 A2 | 9/2002 |
| WO | WO 03/051406 A1 | 6/2003 |
| WO | WO 03/051407 A1 | 6/2003 |
| ZA | 8 505 940 A | 3/1986 |

OTHER PUBLICATIONS

Bowman, et al., "Treatment of Waters Contaminated with BTX and Heavy Metals Using Tailored Zeolites," New Mexico Waste-Management and Education Research Consortium, Technical Completion Report (Project No. WERC-91-41), Mar. 1993, pp. 119-144, U.S.A.
JAPIO abstract 1984-098008 (1984).
HCAPLUS abstract 1984-546140 (1984).
The Merck Index, 12$^{th}$ ed., Merck & Co., Inc., Whitehouse Station, NJ, 1996, p. 683.
Carlson D A Et al.: "Yellowfever mosquitoes. Compounds related to lactic acid that attract females" Journal of Economic Entomology, Entomological Society of America. College Park, Maryland, US, vol. 66, No. 2, 1973, pp. 329-331.
International Search Report from PCT/US03/28717 dated Jan. 28, 2004.
International Search Report from PCT/US03/28723 dated Feb. 4, 2004.

* cited by examiner

METHOD AND COMPOSITION FOR ATTRACTING ARTHROPODS BY VOLATIZING AN ACID

CROSS REFERENCE TO RELATED APPLICATIONS

This application is a divisional of 10/661,724, filed Sep. 12, 2003, now U.S. Pat No. 7,347,994 which is a continuation-in-part of U.S. patent application Ser. No. 10/243,590 filed Sep. 13, 2002, now U.S. Pat. No. 7,922,992 which are incorporated by reference herein in their entirety.

FIELD OF THE INVENTION

The present invention relates to methods of attracting arthropod pests and more particularly to methods of attracting arthropods by volatilizing an acid.

BACKGROUND OF THE INVENTION

Arthropods have plagued humans for centuries. Many types of arthropods (such as mosquitoes, ticks, fleas, sand flies, and midges) are nuisances to human populations because they bite, spread human and veterinary diseases, and cause crop or other property damage. For example, many types of mosquitoes are known to be significant factors in the spread of diseases such as malaria, encephalitis, and West Nile virus. Termites cause almost $2 billion in property damage per year in the United States alone. Therefore, it is important to develop means of controlling populations of arthropods to control the spread of disease and minimize property damage.

A first step to controlling arthropod populations often involves attracting the arthropods in an area to a specific location. Once narrowed to a location, the arthropods can be trapped, killed, or otherwise treated to affect the spread of present and future generations. Attractants can also be used to divert arthropods from a certain location, or for research purposes.

Many arthropods, such as mosquitoes, fleas, and ticks, are naturally attracted to humans and other animals. Light and carbon dioxide are two of the more commonly employed attractants. Other volatile compounds such as L-lactic acid, octenol, acetone, and pheromones have also been used as mosquito attractants.

There is a need in the art to provide a better method for attracting arthropods in large quantities beyond what is feasible using prior art methods.

SUMMARY OF THE INVENTION

The present invention provides a method and composition for attracting arthropods (e.g., mosquitoes) by using a volatile acid (e.g., a humidified volatile acid) in gaseous form. Such volatile acids have been found to be arthropod attractants and, when combined with carbon dioxide, provide greater attraction than carbon dioxide alone. The volatile acid precursor can be provided adjacent an arthropod trapping device and at least a portion of the attracted arthropods can be trapped. Alternatively, the humidified volatile acid precursor can be used in conjunction with a pesticide and the pesticide can be used to kill at least a portion of the attracted arthropods. Alternatively, carbon dioxide gas can be forced over an impregnate bed which may be, for example, zeolites impregnated with a volatile acid and optionally water in a packed bed.

In one embodiment of the invention, the arthropods are attracted by exposing a volatile acid precursor to water to produce a volatilized acid. Preferably, the volatile acid precursor combines with water to produce an acid such as hydrogen chloride or HBr. In accordance with this embodiment, the volatile acid precursor can be a hydrate of ferric chloride such as ferric chloride hexahydrate. The volatile acid precursor can be impregnated in a carrier and can be provided in a gas permeable sachet. The volatile acid precursor can be exposed to water, for example, through exposure to water vapor in the atmosphere, the intentional addition of liquid water, or contact with water produced by a chemical reaction.

In accordance with the invention, a humidified volatized acid can be combined with carbon dioxide to enhance the ability of the humidified volatized acid to attract arthropods. The carbon dioxide can be provided, for example, through the use of carbon dioxide canisters, the sublimation of dry ice, the burning of an organic fuel (e.g. propane or butane), or through a chemical reaction (e.g., a chemical reaction involving yeast generators.) Preferably, the carbon dioxide is produced by exposing a carbon dioxide precursor such as a carbonate, bicarbonate or sesquicarbonate (e.g. sodium bicarbonate) to an acid.

In accordance with one embodiment of the invention, at least one of the volatile acid precursor and the carbon dioxide precursor can be impregnated in a carrier. According to one embodiment of the invention, both of the volatile acid precursor and the carbon dioxide precursor can be impregnated in carriers and can further be provided in a gas permeable sachet.

Furthermore, in accordance with the invention, the humidified volatized acid can be created from an acid having low volatility and salt of a volatile acid. In particular, arthropods can be attracted by combining a low volatility acid and a salt of a volatile acid salt in aqueous solution to produce a volatilized acid. Preferably, according to this embodiment, the low volatility acid is L-lactic acid. The preferred volatile acid salt is sodium chloride and the combination produces small amounts of hydrogen chloride as the volatilized acid.

These and other features and advantages of the present invention will become more readily apparent to those skilled in the art upon consideration of the following detailed description, which describes both the preferred and alternative embodiments of the present invention.

DETAILED DESCRIPTION OF THE PREFERRED EMBODIMENTS

In the following detailed description, preferred embodiments are described in detail to enable practice of the invention. Although the invention is described with reference to these specific preferred embodiments, it will be understood that the invention is not limited to these preferred embodiments. But to the contrary, the invention includes numerous alternatives, modifications, and equivalents as will become apparent from consideration of the following detailed description. The term "comprising" and variations thereof as used herein is used synonymously with the term "including" and variations thereof and is an open, non-limiting term. Furthermore, although terms such as "volatile acid precursor", "carbon dioxide precursor", "low volatility acid" and the like are described herein in singular form, these terms can include combinations of these components. For example, although a volatile acid precursor is described herein, it can include more than one volatile acid precursor in combination as described and as claimed.

In accordance with the invention, arthropods are attracted through the use of a humidified volatile acid vapor. Preferably, the volatile acid is an acid such as hydrogen chloride, HBr, $H_2S$, $SO_2$, $SO_3$, acetic acid or $H_3PO_4$.

The volatile acid is preferably produced by exposing a volatile acid precursor to water. Preferably, the volatile acid precursor combines with water to produce an acid such as hydrogen chloride. The volatile acid precursor is typically a salt of an acid and can be provided in hydrated or anhydrous form. Preferably, the volatile acid precursor is a hydrate of ferric chloride such as ferric chloride hexahydrate. The volatile acid precursor can be exposed to water through exposure to water vapor in the atmosphere, the intentional addition of liquid water, or contact with water produced by a chemical reaction. More particularly, in one example, the volatile acid precursor can be exposed to water as water is produced as a by-product of a reaction between ferric chloride and another substance, such as a carbonate salt. Deliquescents, such as $CaCl_2$ and $MgCl_2$ are especially useful in exposing the volatile acid precursor to water.

The volatile acid precursor can be provided in particulate form (e.g., a powder), or can be impregnated in a porous carrier. Preferably, the porous carrier is an inert carrier in the form of carrier particles having pores, channels or the like located therein. In addition, the volatile acid precursor is preferably uniformly impregnated within the porous carrier. Suitable carriers include silica, alumina, zeolite crystals, pumice, diatomaceous earth, bentonite, or clay (e.g. aluminum silicate or kaolin). Preferably, the porous carrier includes diatomaceous earth or zeolite crystals. The volatile acid precursor can be provided in a gas permeable sachet (e.g. a TYVEK® sachet) or can be put into a packed flow through a column.

In one example, the carrier particles include 0.1% to 80% of the volatile acid precursor and more preferably 30 to 70% of the volatile acid precursor by weight.

In accordance with the invention, the volatized acid can be combined with carbon dioxide to enhance the ability of the volatized acid to attract arthropods. The carbon dioxide can be provided through the use of carbon dioxide canisters, through a combustion reaction (e.g. propane combustion) or by the sublimation of dry ice or use of yeast generators. Preferably, the carbon dioxide is produced by exposing a carbon dioxide precursor such as a carbonate, bicarbonate or sesquicarbonate to an acid. Suitable carbon dioxide precursors are described in related U.S. application Ser. No 10/243, 590 filed on Sep. 13, 2002 now U.S. Pat. No. 7,922,992 and preferred carbon dioxide precursors include sodium carbonate and sodium bicarbonate. The carbon dioxide precursors can be provided as a powder or impregnated in a carrier. Suitable carriers and methods of producing impregnated carrier particles are described above and in U.S. application Ser. No. 10/243,590filed on Sep. 13, 2002, now U.S. Pat. No. 7,922,992. The carbon dioxide precursor can be provided in a gas permeable sachet.

In one preferred embodiment of the invention, ferric chloride hexahydrate is used as the volatile acid precursor and sodium bicarbonate is used as the carbon dioxide precursor. As discussed above, other volatile acid precursors and carbon dioxide precursors can be used. In this preferred embodiment, ferric chloride hexahydrate combines with water to produce hydrochloric acid. The hydrochloric acid then reacts with sodium bicarbonate to form carbon dioxide and water. The water of reaction combines with ferric chloride hexahydrate to form more hydrogen chloride. Some of the hydrogen chloride reacts with the sodium bicarbonate to produce more carbon dioxide and water, while some of the hydrogen chloride volatilizes and leaves the reaction mixture along with the carbon dioxide. Some of the water also leaves as water vapor that humidifies the gas mixture.

The volatized acid can also be produced from an acid having low volatility to attract mosquitoes in accordance with the invention. In this embodiment, a low volatility acid is combined with a salt of a volatile acid. The interaction of these materials produces a volatile acid such as hydrogen chloride. Suitable low volatility acids include weak organic acids such as L-lactic acid. Preferably, the low volatility acid is L-lactic acid and the salt is sodium chloride, KCl, LiCl, $MgCl_2$, or $CaCl_2$.

Preferably, the low volatility acid and the volatile acid salt are used in a concentrated aqueous solution. For example, the concentrated aqueous solution can include greater than 1M of each of the low volatility acid and the volatile acid salt. In particular, at the higher concentration, an ion exchange occurs such that, for example, NaCl and lactic acid produce sodium lactate and HCl, a volatile acid. One method of producing the concentrated aqueous solution is to begin with a less concentrated solution and to allow the water in the solution to evaporate.

As a result of the invention, arthropods are attracted to the volatilized acid, and the attracted arthropods can be diverted from a specific area, trapped, killed, or otherwise modified to reduce the overall population of the arthropod in the area. For example, the volatile acid precursor and other components discussed above can be provided adjacent to a trap for arthropods, e.g., a mosquito trap. Alternatively, carbon dioxide gas can be pushed through a bed of acid impregnated media, or acid releasing media to effectively humidify and acidify the carbon dioxide gas. Specifically, the volatile acid precursor can be provided in or on the trapping device. The attracted arthropods can also be killed using a pesticide. For example, the volatile acid precursor and other components discussed above can be mixed with a pesticide for use in the invention.

The invention will now be further described by the following non-limiting examples.

EXAMPLE 1

Ferric Chloride Activation

100 Aedes aegypti (AE) mosquitoes were placed into an olfactometer unit. For each test, the mosquitoes were exposed to two sets of stimuli for a collection period of 3 minutes. The mosquitoes could choose between the stimuli or not respond. The data is reported in Table 1.

For the first test, ferric chloride hexahydrate was impregnated on diatomaceous earth and was activated with a moisture containing substance to form the first stimulus center. This material released water and trace amounts of hydrochloric acid, HCl. The second stimulus center in this test was a blank (no chemical stimulus).

For the second test, dry carbon dioxide was fed at 5 ml/min from a standard gas cylinder as the first stimulus center. The second stimulus center in this test was a blank (no chemical stimulus). The carbon dioxide alone attracted some of the insects but in general did not draw significant numbers.

For the third test, ferric chloride hexahydrate was impregnated on diatomaceous earth and was activated with a moisture containing substance to form the first stimulus center. This material released water and trace amounts of hydrochloric acid, HCl. The second stimulus center was dry carbon dioxide fed at 5 ml/min from a standard gas cylinder. The data shows a higher percentage of mosquitoes responded to the stimulus provided by the activated ferric chloride material. In comparison with carbon dioxide, the ferric chloride impregnate attracted substantially more mosquitoes.

TABLE 1

Average Percent AE Attracted

| Stimulants | Stimulant 1 - Avg. % attracted | Stimulant 2 - Avg. % attracted |
|---|---|---|
| Activated Ferric Chloride v. Blank | 51 | 1 |
| $CO_2$ (Dry) v. Blank | 21 | 0 |
| Activated Ferric Chloride v. $CO_2$ | 70 | 12 |

EXAMPLE 2

Activated Ferric Chloride Hexahydrate with Sodium Bicarbonate Sachet

As with Example 1, 100 AE mosquitoes were placed into an olfactometer unit. For each test, the mosquitoes were exposed to two sets of stimuli for a collection period of 3 minutes. The mosquitoes could choose between the stimuli or not respond. The data is reported in Table 2.

For the first test, dry carbon dioxide was fed at 5 ml/min from a standard gas cylinder as the first stimulus center. The second stimulus center in this test was a blank (no chemical stimulus).

For the second test, ferric chloride hexahydrate impregnated on diatomaceous earth and sodium bicarbonate powder were contained in a sachet. The sachet was activated by combining the two powders stimulating a chemical reaction that released carbon dioxide, water and trace amounts of hydrochloric acid, forming the first stimulus center. The reaction produces by-product water that stimulates hydrochloric acid production from the ferric chloride. The sachet was designed to release $CO_2$ at a rate of 5 ml/min over the collection period. The second stimulus center in this test was a blank (no chemical stimulus).

For the third test, a sachet containing ferric chloride hexahydrate impregnated on diatomaceous earth and sodium bicarbonate powder, similar to the sachet used in the second test, was activated with a moisture-containing substance to release carbon dioxide water and trace amounts of hydrochloric acid, forming the first stimulus center. The reaction produces by-product water that stimulates hydrochloric acid production from the ferric chloride. The second stimulus center was carbon dioxide fed at 5 ml/min from a standard gas cylinder.

The data shows the majority of mosquitoes responded to the stimulus provided by the carbon dioxide and hydrochloric acid releasing sachet. In comparison with carbon dioxide alone, the sachet attracted substantially more mosquitoes.

TABLE 2

Average Percent AE Attracted

| Stimulants | Stimulant 1 - Avg. % attracted | Stimulant 2 - Avg. % attracted |
|---|---|---|
| $CO_2$ (Dry) v. Blank | 21 | 0 |
| $CO_2/HCl/H_2O$ Sachet v. Blank | 96 | 0 |
| $CO_2/HCl/H_2O$ Sachet v. $CO_2$ | 93 | 2 |

EXAMPLE 3

Activated Ferric Chloride Hexahydrate with Sodium Bicarbonate Sachet

As with Examples 1 and 2, 100 AE mosquitoes were placed into an olfactometer unit. For each test, the mosquitoes were exposed to two sets of stimuli for a collection period of 3 minutes. The mosquitoes could choose between the stimuli or not respond. The data is reported in Table 3.

For the first test, ferric chloride hexahydrate impregnated on a diatomaceous earth was activated with a moisture containing substance to form the first stimulus center. This material released water and trace amounts of hydrochloric acid, HCl. The second stimulus center in this test was a blank (no chemical stimulus).

For the second test, a sachet containing ferric chloride hexahydrate impregnated diatomaceous earth and sodium bicarbonate powder was used, similar to the sachet used in Example 2. The sachet was activated by combining the two powders stimulating a chemical reaction that released carbon dioxide, water and trace amounts of hydrochloric acid, forming the first stimulus center. The reaction produces by-product water that stimulates hydrochloric acid production from the ferric chloride. The sachet was designed to release carbon dioxide at a rate of 5 ml/min. The second stimulus center in this test was a blank.

For the third test, a sachet identical to that used in the second test and containing ferric chloride hexahydrate impregnated on diatomaceous earth and sodium bicarbonate powder was activated, forming the first stimulus center. The second stimulus center in this test was ferric chloride hexahydrate impregnated on diatomaceous earth and activated with a moisture containing substance to form hydrogen chloride, as in Example 1.

For the fourth test, a sachet containing ferric chloride hexahydrate impregnated on diatomaceous earth and sodium bicarbonate powder, identical to that in the first test, was activated to form the first stimulus center. The second stimulus center had two components. The first component was activated ferric chloride hexahydrate impregnated on diatomaceous earth, as in Example 1. The second component of the second stimulus center was dry carbon dioxide fed at 5 ml/min from a standard gas cylinder.

The data shows the majority of mosquitoes responded to the stimulus provided by the carbon dioxide-releasing reactions. The sachet was also compared to the activated ferric chloride with a separate dry carbon dioxide source (test 3). The activated ferric chloride did enhance the attractive capability of the carbon dioxide alone. However, the sachet was substantially more stimulating to the mosquitoes than any of the other stimulus centers.

TABLE 3

Average Percent AE Attracted

| Stimulants | Stimulant 1 - Avg. % attracted | Stimulant 2 - Avg. % attracted |
|---|---|---|
| Activated Ferric Chloride v. Blank | 51 | 1 |
| $CO_2/HCl/H_2O$ Sachet v. Blank | 96 | 0 |
| $CO_2/HCl/H_2O$ Sachet v. Activated Ferric Chloride alone | 54 | 34 |
| $CO_2/HCl/H_2O$ Sachet v. Activated Ferric Chloride plus $CO_2$ | 63 | 26 |

EXAMPLE 4

As with Examples 1, 2 and 3, 100 Aedes aegypti (AE) mosquitoes were placed into an olfactometer unit. For each test, the mosquitoes were exposed to two sets of stimuli for a collection period of 3 minutes. The data is reported in Table 4.

In these tests, dry $CO_2$, flowing at 5 mL/min was passed through either a hollow tube, or through a cartridge containing a bed of porous media impregnated with either water, HCl solution, or ferric chloride hexahydrate. The point at which the $CO_2$ entered the olfactometer was considered a stimulus center.

For the first test, the first stimulus center received $CO_2$ that had flowed through a bed of ferric chloride hexahydrate on porous carrier. The second stimulus center was blank (no chemical stimulus).

For the second test, the first stimulus center received $CO_2$ that had flowed through a hollow tube. The second stimulus center was blank (no chemical stimulus).

For the third test, the first stimulus center received $CO_2$ that had flowed through a bed of water impregnated in a porous carrier. The second stimulus center was blank (no chemical stimulus).

For the fourth test, the first stimulus center received $CO_2$ that had flowed through a bed of HCl solution on porous carrier. The second stimulus center received $CO_2$ that had flowed through a bed of water impregnated in a porous carrier.

For the fifth test, the first stimulus center received $CO_2$ that had flowed through a bed of ferric chloride hexahydrate impregnated in a porous carrier. The second stimulus center received $CO_2$ that had flowed through a bed of water impregnated in a porous carrier.

For the sixth test, 5 mL/min of $CO_2$ was passed through a hollow tube and blown over the surface of water in a Petri dish to form the first stimulus center. Also, 5 mL/min of $CO_2$ as passed through a hollow tube to form the second stimulus center.

The data shows that $CO_2$ (dry) is an attractant for mosquitoes. However, $CO_2$, humidified $CO_2$, or humidified $CO_2$ containing HCl are better attractants than dry $CO_2$. The data also shows that humidified $CO_2$ containing HCl is a better attractant than humidified $CO_2$.

TABLE 4

| | Average Percent AE Attracted | |
|---|---|---|
| Stimulants | Stimulant 1 - Avg. % attracted | Stimulant 2 - Avg. % attracted |
| $CO_2$/cartridge of carrier impregnated with Ferric chloride vs blank | 93 | 1 |
| $CO_2$ (dry)/tube vs blank | 15 | 0 |
| $CO_2$/cartridge of carrier impregnated with water vs blank | 88 | 0 |
| $CO_2$/cartridge of carrier impregnated with HCl vs $CO_2$/cartridge of carrier impregnated with water | 73 | 13 |
| $CO_2$/cartridge of carrier impregnated with Ferric chloride vs $CO_2$/cartridge of carrier impregnated with water | 48 | 40 |
| $CO_2$ flowing over water surface versus $CO_2$ (dry) | 43 | 7 |

It is understood that upon reading the above description of the present invention and reviewing, one skilled in the art could make changes and variations therefrom. These changes and variations are included in the spirit and scope of the following appended claims.

That which is claimed:

1. A composition for attracting arthropods comprising:
   a volatile acid precursor comprising a metal salt that is acidic when combined with water, said volatile acid precursor is impregnated in a porous carrier selected from the group consisting of silica, alumina, zeolite crystals, pumice, diatomaceous earth, bentonite, clay, and combinations thereof; and
   a carbon dioxide precursor comprising a compound selected from the group consisting of carbonates, bicarbonates, sesquicarbonates, and combinations thereof.

2. The composition according to claim 1, wherein the carbon dioxide precursor is impregnated in the same or a different porous carrier.

3. The composition according to claim 1, wherein the volatile acid precursor produces hydrogen chloride upon exposure to water.

4. The composition according to claim 3, wherein the volatile acid precursor is a hydrate of ferric chloride.

5. The composition according to claim 1, wherein the volatile acid precursor and the carbon dioxide precursor are contained in a gas permeable sachet.

6. The composition according to claim 1, further comprising a pesticide.

7. The composition according to claim 6, wherein said pesticide is combined with the volatile acid precursor and the carbon dioxide precursor.

8. The composition according to claim 1, wherein the volatile acid precursor is ferric chloride hexahydrate and the carbon dioxide precursor is sodium bicarbonate.

* * * * *

UNITED STATES PATENT AND TRADEMARK OFFICE
CERTIFICATE OF CORRECTION

PATENT NO. : 8,709,396 B2  
APPLICATION NO. : 12/032885  
DATED : April 29, 2014  
INVENTOR(S) : Tenney et al.

Page 1 of 1

It is certified that error appears in the above-identified patent and that said Letters Patent is hereby corrected as shown below:

Title page,  
Item (73) Assignee: "Premark FEG L.L.C., Wilmington, DE (US)" should read --ICA TriNova, LLC, Forest Park, GA (US)--.

Signed and Sealed this  
Nineteenth Day of August, 2014

Michelle K. Lee  
*Deputy Director of the United States Patent and Trademark Office*